US007601297B2

United States Patent
Gygax et al.

(10) Patent No.: US 7,601,297 B2
(45) Date of Patent: Oct. 13, 2009

(54) FRAGRANCE DISPENSING DEVICE (75) Inventors: Hans Rudolf Gygax, Bad-Ragaz (CH); Norbert Schmid, Uerikon (CH)

(73) Assignee: Givaudan SA, Vernier (CH)

( * ) Notice: Subject to any disclaimer, the term of this patent is extended or adjusted under 35 U.S.C. 154(b) by 225 days.

(21) Appl. No.: 10/521,716

(22) PCT Filed: Jul. 22, 2003

(86) PCT No.: PCT/CH03/00497

§ 371 (c)(1),
(2), (4) Date: Jan. 19, 2005

(87) PCT Pub. No.: WO2004/009142

PCT Pub. Date: Jan. 29, 2004

(65) Prior Publication Data

US 2005/0244307 A1 Nov. 3, 2005

(30) Foreign Application Priority Data

Jul. 24, 2002 (GB) .................................. 0217116.3

(51) Int. Cl.
*A61L 9/12* (2006.01)
*A61L 9/04* (2006.01)
(52) U.S. Cl. .......................................... 422/5; 422/124
(58) Field of Classification Search ........................ None
See application file for complete search history.

(56) References Cited

U.S. PATENT DOCUMENTS

| 3,795,438 | A | | 3/1974 | Westenholz et al. ............ 352/85 |
| 4,017,030 | A | * | 4/1977 | Coplan et al. .................. 239/44 |
| 4,445,641 | A | | 5/1984 | Baker et al. ..................... 239/6 |
| 5,266,492 | A | * | 11/1993 | Wood et al. .................... 436/34 |
| 5,573,984 | A | | 11/1996 | Breitenbucher et al. ....... 501/39 |

(Continued)

FOREIGN PATENT DOCUMENTS

FR 2771930 6/1999

(Continued)

OTHER PUBLICATIONS

Bengård A and Colmsjö A; Ga"Gas Chromatographic Methods for the Assessment of Binary Diffusion Coefficients for Compounds in Gas Phase"; *Journal of Chromatography*, 522 (1990) 277-284.

(Continued)

*Primary Examiner*—Elizabeth L McKane
(74) *Attorney, Agent, or Firm*—Norris McLaughlin & Marcus, PA; Christa Hildebrand, Esq.

(57) ABSTRACT

A fragrance cartridge comprising a reservoir containing a fragrance material and provided with channels to permit ingress of carrier gas into the reservoir and egress of fragrance-containing carrier gas from the reservoir, the channels being defined by capillaries having internal diameter and length dimensions sufficient to act as closure means to prevent, or substantially prevent, leakage of fragrance from the reservoir into a head space external of the cartridge when carrier gas flow is interrupted. The cartridge can be used for example to enhance the sensorial perception of a viewer, listener or consumer of an audio and/or visual performance or presentation, by passing fragrance borne on the carrier into a head space local to the listener, viewer or consumer.

13 Claims, 5 Drawing Sheets

U.S. PATENT DOCUMENTS

| | | | |
|---|---|---|---|
| 6,135,431 A | 10/2000 | Mühlmel et al. | 261/101 |
| 6,371,165 B1 | 4/2002 | Manne | 137/883 |
| 7,261,812 B1 * | 8/2007 | Karp et al. | 210/198.2 |
| 2002/0114744 A1 * | 8/2002 | Chiao et al. | 422/124 |

FOREIGN PATENT DOCUMENTS

| | | |
|---|---|---|
| GB | 1 555 554 A | 11/1979 |
| GB | 2 042 340 A | 9/1980 |

OTHER PUBLICATIONS

Martin Quack, "Molekulare Thermodynamik und Kinetic: Teil 1"; *Chemische Reaktionskinetik*, Ch 8 at p. 216-225, VDF publication 1986.

* cited by examiner

FRAGRANCE DISPENSING DEVICE

This is an application filed under 35 USC 371 of PCT/CH03/00497.

BACKGROUND OF THE INVENTION

The invention is concerned with fragrance cartridges for storing fragrances, and for releasing them on demand by means of a stream of carrier gas that may flow through the cartridges.

Odour presentation has typically been carried out using scent bottles and absorbent paper smelling strips, scent pens or olfactometers. These presentation methods suffer on the one hand from inaccurate dosing and the possibility of contamination of surfaces with liquid samples, and on the other hand from the complexity of the dosing device. Recently, fragrance cartridges have been proposed that can store fragrance for long periods of time before releasing the fragrance in a time-dependent and controlled manner by means of a flow of carrier gas.

Fragrance cartridges are known in FR 2771930. They are described as being capable of releasing fragrance on a stream of carrier gas in a time-controlled manner. A cartridge consists of a cylindrical reservoir of uniform cross section. The fragrance is contained in the reservoir and is supported on a suitable carrier material. Closure of the reservoir to prevent fragrance loss during storage is provided by flexible membrane disks that seal both ends of the reservoir. Fragrance is released when the membranes are punctured with hollow needles or cannulae, whereupon fragrance is permitted to flow out of the reservoir and through the needles or cannulae on a stream of carrier gas.

The prior art does not disclose any information as to the dimensional requirements of the cartridges needed to facilitate storage and release of fragrance from said cartridges. Storage and release is simply predicated on the puncture and re-sealing of the flexible membranes using cannulae. Whereas fragrance can be released in a satisfactory manner on a carrier gas stream from such cartridges by such measures, when gas flow is interrupted, fragrance continues to leak from the cannulae and strong fragrant head space around the cannulae can be detected. Whereas this evolution of unwanted head space can be remedied by removing the cannulae, the repetitive puncturing and removal inevitably compromises the sealing properties of the membranes, leading eventually to failure of sealing properties and leakage.

Furthermore, removal of cannulae requires a mechanical operation. If this is done by manual intervention, the process of switching from the emission of one fragrance accord to another is slow and laborious, rendering the cartridge impractical if rapid entry and re-entry into the reservoir is required to release fragrances in a responsive time-dependant manner. Yet, if automated means for this operation are provided, it adds to the complexity of the design of the cartridge, or means interacting with the cartridge thereby adding to the expense of achieving fragrance delivery.

There remains a need to provide fragrance cartridges that are capable of releasing fragrance material on demand and in a time-controlled manner on a stream of carrier gas, and yet when inactive, they are able to store fragrance essentially without leakage by employing means that are capable of mass-production at low cost.

A study of the diffusion behaviour of fragrances revealed that displacement per unit time of even very diffusive fragrance materials was, remarkably, rather small. It was also surprisingly found that if fragrance molecules were permitted to diffuse through narrow capillaries, even the most diffusive molecules were so constrained that the capillaries acted essentially as if they were closed. This allowed the development of a very simple means of actuating and interrupting flow of a fragrance from a fragrance-containing reservoir without the need for mechanical intervention to interrupt flow.

BRIEF SUMMARY OF THE INVENTION

Therefore the invention provides in a first aspect a fragrance cartridge comprising a reservoir containing a fragrance material and provided with inlet and outlet channels to permit ingress of carrier gas into the reservoir and egress of fragrance-containing carrier gas from the reservoir, the channels being defined by capillaries having internal diameter and length dimensions sufficient to act as closure means to prevent, or substantially prevent, leakage of fragrance from the reservoir into a head space external of the cartridge when carrier gas flow is interrupted.

By the phrase "substantially prevent", in relation to fragrance leakage, it is meant that to the extent that any fragrance leaks, the rate of leakage is so low that any concentration of leaked fragrance emanating into a head space external of the cartridge, or device containing a cartridge, is below the detection level of a user. As a practical guide and without limiting the invention in any way, the cartridge should be configured such that the fragrance leakage does not exceed a rate of 400 ng per second.

The cartridges according to the present invention may be connected to a device containing pump means in order to release a fragrance material on demand thereby to create a head space of fragrance external of the cartridge or device, which can be sensed by a user. Furthermore, if carrier gas flow is actuated and interrupted according to a pre-determined sequence, the outlet capillaries act essentially as valves to prevent or permit fragrance release in a controlled and responsive manner. As such, an odourant can be delivered accurately to a head space when required and does not deliver any leaked fragrance to the head space, thereby avoiding head space contamination after gas flow is interrupted. Accordingly, when a series of cartridges containing different fragrance materials are linked to a device controlling the flow of carrier gas through said cartridges in a time-controlled manner, different fragrances may be released in a pre-determined sequence. This opens the possibility of actuating and interrupting gas flow through a given cartridge in accordance with a signal received from audio/visual equipment, thereby to synchronise fragrance release with certain visual and/or acoustic signals such that a consumer, viewer or listener can listen to, and/or watch a performance such as a film, a piece of music or a presentation, whilst receiving corresponding odour impressions in his or her surrounding head space. Such responsiveness necessary to realise this synchronised effect has not hitherto been possible using known cartridges that require mechanical disconnection and reconnection of cannulae from a reservoir in order to switch fragrance release on and off. Or at least, this could not be achieved in a cost effective manner.

It is an important aspect of the present invention that the inlet/outlet capillaries must be of an appropriate inner diameter and length to act as closure means. Once apprised of the surprising discovery that these capillaries can act substantially to prevent fragrance leakage by diffusion, it is a simple matter for the skilled person to select the diameter and length of the capillaries for its particular purpose. Thus, a fragrance material that has a very high vapour pressure and a very low detection threshold can be taken and there can be calculated the maximum diameter and minimum length of the capillaries that still permit of a reduction of fragrance leakage to levels below that of detection in an external head space. Exemplary of such fragrance materials are ethyl acetate, myrcene and eucalyptol.

In order to assess whether levels of fragrance leakage are detectable or not, a relevant head space volume should be defined. Given that cartridges of the present invention are to be used primarily to emit small amounts of fragrance into small head spaces local to a user, a relevant head space for this determination is taken to be one liter. This also takes into consideration that, in general, an adult person aspires air at a rate of 8 to 10 liters per minute. As such, the relevant head space will be aspired during 6 to 8 seconds. Accordingly, under such stringent conditions, by determining the maximum internal diameter, and minimum length needed to prevent substantial leakage of the aforementioned fragrance materials, we can produce cartridges that will substantially prevent the leakage of any fragrance materials that are available in the palette of perfumers.

Thus, the invention provides in another of its aspects a method of forming cartridges comprising the step of determining the dimensions of the capillaries in order to ensure that they act as effective closure means within the meaning of the present invention, in accordance with the methodology disclosed hereinunder. It is another aspect of the invention to provide a method of fragrancing a head space comprising the step of selecting a fragrance cartridge according to the selection criteria set forth hereinbelow.

It is well known that displacement of molecules in a gas may occur as a result of fluctuating air currents and by diffusion. In narrow capillaries, there is little or no influence of air currents and so molecular displacement is essentially controlled by diffusion. Molecules diffuse from a point of high concentration to a point of lower concentration in a series of random movements. These random movements occur as a result of collisions between a gas molecule and its neighbours. Through this random movement, a gas molecule will have a characteristic displacement per unit time that is related to its intrinsic properties such as its size, mass and polarity. The tendency of a given gas molecule towards displacement may be expressed in terms of its Diffusion Coefficient (D) and is expressed in units of $cm^2/s$. The Diffusion Coefficient for a given molecule can be calculated following the methodology of Bemgård A and Colmsjö A, Gas Chromatographic Methods for the Assessment of Binary Diffusion Coefficients for Compounds in Gas Phase J Chromatogr. 522 (1990) 277-284. This is a sophisticated calculation model that has been validated with experimental data for a large palette of molecules.

Presented with the Diffusion Coefficient of a given fragrance material, it is possible to calculate the diffusion distance per unit time for a relevant diffusion symmetry. By "relevant diffusion symmnetry" we assume a linear diffusion model, for example as described in Martin Quack, Molekulare Thermodynamik und Kinetic: Teil 1. Chemische Reaktionskinetik; Ch 8 at p 216-225, VDF publication 1986. This model assumes that a molecules of a gas move in one dimension along a tube. According to the model, the distance the molecule will travel, $r_{diff}$, is given by the formula $$r_{diff} = \sqrt{2Dt}$$

wherein D is the Diffusion Coefficient ($cm^2/s$) and t is time (seconds). Thus, measuring D at ambient temperature and pressure, one can calculate the diffusion distance in one second along the tube for a given fragrance material.

Further, for a given internal diameter of capillary, the concentration of a fragrance material in that capillary can be described as a function (see equation below) of the distance from the origin (r=0), which is set as the point where the reservoir and capillary join. Still further, it is within the realm of common general knowledge that diffusion of a gas is defined by the two Fick Laws, defined by general differential equations, and that in the given case have two well defined boundary conditions: First, at the capillary inlet (origin) the concentration c(r=0) of fragrance is taken to be the vapour pressure. Second, for a capillary with infinite length, the concentration at r=infinity is zero. Assuming that at the end of the capillary with a length L, at its outlet, diffusing molecules will immediately experience turbulence and thus be mixed with ambient pure air, the boundary condition for c(L) can be set to zero. Therefore, the solution of the stationary diffusion equation provides the following concentration gradient in the capillary:

$$C(r) = C(r=0) + 1/r[(C(r=L) - C(r=0))/L]$$

wherein

C(r) is the concentration at a distance r from the origin,

C(r=0) is the head space concentration of fragrance material in reservoir, and

C(r=L) is set to zero.

Therefore, $C(L-r_{diff})$ represents the concentration of fragrance in the portion of the capillary a distance $r_{diff}$ measured from the outlet, and is therefore relevant for the leakage rate out of the capillary. It is possible to calculate the leak-rate (mass-loss per second) by multiplying this concentration by the volume fragment of the capillary with length $r_{diff}$ and the area formed by the inner capillary diameter ($V_{diff} = \Pi d^2/4$).

From this calculated leak-rate, the amount of fragrance being leaked into the head space per second may be determined. Therefore, if a dilution of this amount of fragrance into a head space of 1 liter is assumed, it is easy to determine whether the capillary dimensions are sufficient to prevent a Sensory Threshold Concentration within the head space.

In this manner, the present invention defines a simple method of determining appropriate dimensions for a cartridge without the skilled person having to resort to undue experimentation. Furthermore, a comparison of the theoretical assessment presented above with experimental data for ethyl acetate, myrcene and eucalyptol and found excellent correspondence of theory and experimental data as is shown in Table 1 below.

| Molecule | d [mm] | L [mm] | diffusion · distance (r) [mm/s] | Vapour pressure [ug/l] | Sensory Threshold [ng/l] | Experiment Leak rate [ng/s] | Calculation Leak rate | OV |
|---|---|---|---|---|---|---|---|---|
| Ethyl Acetate | 1.2 | 16.5 | 4.0 | 414202 | 54 | 300 | 397 ng/s | 6 |

-continued

| Molecule | d [mm] | L [mm] | diffusion · distance (r) [mm/s] | Vapour pressure [ug/l] | Sensory Threshold [ng/l] | Experiment Leak rate [ng/s] | Calculation Leak rate | OV |
|---|---|---|---|---|---|---|---|---|
| Ethyl Acetate | 0.4 | 30 | 4.0 | 414202 | 54 | 14 ng/s | 18 ng/s | <1 |
| Myrcene | 1.2 | 16.5 | 3.4 | 13736 | 136 | 26 | 14 | ~1 |
| Myrcene | 0.4 | 30 | 3.4 | 13726 | 136 | 1.8 | 0.7 | <1 |
| Eucalyptol | 1.2 | 16.5 | 3.3 | 14980 | 154 | 26 | 12 | ~10 |
| Eucalyptol | 0.4 | 30 | 3.3 | 14980 | 154 | not detectable | 0.8 | <1 |

Referring to Table 1, the vapour pressure and Sensory Detection Threshold are parameters that are characteristic of fragrance materials and are well known persons skilled in the perfumery art. The Odour Value ("OV") of a fragrance material is dimensionless and is provided by the ratio of the concentration in the head space divided by its Sensory Threshold Concentration. An OV of unity (1) is taken to mean that the Threshold Concentration has been reached such that 50% of the population will be able to detect the fragrance in the head space, i.e. its detection by a person having mean sensing ability is purely to chance. The Threshold Concentration can be measured according to a standard test method ASTM E1432-91, and is measured either by olfactometry means or by using sniff-bottles and allowing panelists to assess the head space presented.

These results demonstrate that for ethyl acetate, which represents one of the most diffusive materials in the palette of a perfumer, for a diameter of 1.2 mm the length of 16.5 mm is too short as the leakage rate is rather high, such that the "OV" is 6 times above threshold. However, when the diameter is reduced to 0.4 mm, the leakage is undetectable. The results for eucalyptol follow a similar pattern as for ethyl acetate, but myrcene shows a non-detectable leakage for either outlet tube.

These results further demonstrate that the present invention describes a simple and reliable method of calculating cartridge dimensions based on Diffusion Coefficient data of fragrance materials, which are either known or can be measured according to techniques known in the art. In fact, if an outlet capillary length of about 30 mm is an acceptable length in terms of the overall dimensions of a cartridge containing such capillaries, the present invention demonstrates that all fragrance materials known to perfumers can be essentially trapped in a cartridge according to the present invention having a capillary internal diameter of 0.4 mm or less. Preferred cartridges according to the present invention have internal capillary diameters of 0.1 to 0.4 mm. Preferred cartridges according to the invention have capillary lengths of about 20 to 30 mm.

The dimensions of the inlet and outlet capillaries however is a matter of choice for the skilled person, depending on the shape and configuration of the device to contain or connect with the cartridge or cartridges. Furthermore, the invention is not limited to any particular length or diameter of capillary other than is purely necessary for the capillary to fulfil its stated function. The cartridge may otherwise be any shape or configuration suitable to the its intended end use, and suited to the device it is to be inserted in, or connected to. If economy of space is an issue, a rather short capillary length may be desired, and the internal diameter of the capillary would have to be narrowed accordingly.

The latitude to reduce the diameter of the inlet and outlet capillaries does nevertheless have limitations. The capillaries' diameter should not be so narrow that the pressure of carrier gas will be prohibitively high in order to force it through the cartridge. The pressure of carrier gas must be sufficient to expel a saturated head space of fragrance material contained in the reservoir, through the outlet tube and into the external head space in a short period of time, e.g. 2 to 5 seconds but it should preferably not exceed a pressure of about 200 mbar over atmospheric pressure. Above this pressure, the vapour pressure of fragrance components in the reservoir may be altered to an extent that it is no longer possible to generate a saturated head space in the reservoir quickly enough to emit fragrance in the desired manner. Having regard to these factors the skilled person would have no difficulty in determining the minimum acceptable internal diameter for the capillaries. In particular, to avoid gas pressure problems, the minimum internal diameter of the tube should be in the order of about 0.1 millimeters. However, it is unlikely that one would need to resort to such a small diameter, unless there was a need to drastically reduce the tube length, for example in order to produce a very miniaturised version of the cartridge. Even then, miniaturisation may be possible whilst maintaining capillary length simply by employing the expedient of coiling the capillary.

Generally, whereas small diameter capillaries, e.g. 0.1 to 0.4 mm are preferred because the cartridges are primarily intended to be used to generate only small head spaces, e.g. about one liter, containing small amounts of fragrance material, nevertheless, if fragrancing of larger head spaces is required, large volumes of carrier gas will need to pass through the cartridges in a relatively short space of time in order to provide the larger concentrations of fragrance needed to saturate larger external head spaces. Therefore, larger internal diameters of capillaries will be required, i.e. greater than 1.2 mm, and up to about 0.5 cm in order to accommodate these higher carrier-gas flows. In such a case, the length of the tube will have to be increased accordingly. Once again, if economy of space is an issue, the capillaries may be coiled.

Preferably, the inlet capillary should be similarly configured as the outlet capillary in order to prevent leakage of fragrance material during storage of the cartridge, or during periods when no carrier gas flows through the cartridge. Preferably, disposed within the inlet capillary is a plug of activated carbon. This has the advantage of purging inlet carrier gas of impurities that may have organoleptic properties and adversely influence the fragrance accord expressed from the cartridge. The plug has the additional advantage that in use, it may prevent any flow of fragrance material up the tube in the event of a back-pressure event caused by malfunction of a carrier gas pump.

In a similar fashion, the outlet tube may contain a plug to prevent any particulate reservoir carrier material from being ejected from the reservoir and out through the outlet capillary under pressure. Such a plug may be formed of a suitably inert material such as cotton or quartz glass wool.

Whereas the cartridges of the present invention prevent detectable leakage of fragrance materials, nevertheless it remains that in the case of some of the most diffusive fragrance materials there will be quite a large fragrance loss over extended periods of storage. Notwithstanding that for the vast majority of fragrances, the loss of fragrance over prolonged periods of time is negligible. However, insofar as there may be a problem with exhaustion of the most diffusive of fragrance materials during storage, in particular when the reservoirs only contain low concentrations of these materials, one can take the additional precaution of adding a sealing tape or the like, across the inlets and outlets of the capillaries that form gas-tight seals. Such tapes may be present during storage and be removed or punctured shortly before use.

Aside from the very diffusive of fragrance materials described above, the present invention may be used to deliver all types of fragrance materials, assured that there will be no leakage, or substantially no leakage when carrier gas flow is interrupted. And yet the cartridges can be small in size such that it can be miniaturised and still permit of acceptable carrier-gas flows at acceptable pressures to enable saturated head spaces of fragrance materials to be generated quickly on demand. This means that any type of fragrance material available to the perfumer can be employed in the present invention, such as those classes of known compounds, e.g. acids, esters, alcohols, aldehydes, ketones, lactones, nitriles, ethers, acetates, hydrocarbons, sulfur- nitrogen- and oxygen-containing heterocyclic, polycyclic and macrocyclic compounds, as well essential oils of natural or synthetic origin. Such fragrance materials are described, for example, in S. Arctander Perfume Flavors and Chemicals Vols. 1 and 2, Arctander, Montclair, N.J. USA 1969. The fragrances optionally may comprise odourless liquids such as dipropylene glycol, propylene glycol, diethylphtalate, benzyl benzoate, triethylcitrate, isopropylmyristate, carbitol, and hexylene glycol, or mixtures thereof.

Illustrative examples of fragrances selected from these general classes include C6 hexylic, acetophenone, alcohol C6 hexylic, aldehyde C7 heptylic, aldehyde C9 isononylic, allyl caproate, allyl oenanthate, amyl butyrate, amyl vinyl carbinol, anapear, benzaldehyde, benzyl formate, benzyl methyl ether, bomyl acetate liquid, butyl acetate, camphene, carbitol, citronellal, cresyl methyl ether para, cyclal C, cymene para, decenal-4-trans, delta-3 carene, diethyl malonate, dihydro anethole, dihydro myrcenol, dimethyl octenone, dimetol, dimyrcetol, dipentene, estragole, ethyl acetate, ethyl acetoacetate, ethyl amyl ketone, ethyl benzoate, ethyl butyrate, ethyl caproate, ethyl isoamyl ketone, ethyl isobutyrate, ethyl methyl-2-butyrate, ethyl oenanthate, ethyl propionate, eucalyptol, fenchone alpha, fenchyl acetate, fenchyl alcohol, freskomenthe, geranodyle, guaiacol, hexenal-2-trans, hexenol-3-cis, hexenyl acetate, hexenyl-3-cis butyrate, hexenyl-3-cis formate, hexenyl-3-cis isobutyrate, hexenyl-3-cis methyl-2-butyrate, hexenyl-3-cis propionate, hexyl butyrate, hexyl isobutyrate, hexyl propionate, hydratropic aldehyde, isoamyl propionate, isobutyl isobutyrate, isocyclocitral, isopentyrate, isopropyl methyl-2-butyrate, isopulegol, leaf acetal, lime oxide, limetol, linalool oxide, linalool, manzanate, melonal, menthone, methyl amyl ketone, methyl benzoate, methyl camomille, methyl hexyl ketone, methyl pamplemousse, methyl salicylate, nonanyl acetate, ocimene, octenyl acetate, pandanol, pinene alpha, pinene beta, prenyl acetate, terpinene gamma, terpinolene, tetrahydro citral, tetrahydro linalool, tricyclal, and valerolactone gamma, acetal E, acetal R, acetanisole, adoxal, agrumex, alcohol C10 decylic, alcohol C11 undecylenic, alcohol C12 lauric, alcohol C8 octylic, alcohol C9 nonylic, aldehyde C11 undecylenic, aldehyde C12 undecylic, aldehyde C12 lauric, aldehy, aldehyde iso C11, allyl amyl glycolate, allyl cyclohexyl propionate, ambrinol, amyl benzoate, amyl caproate, amyl cinnamic aldehyde, amyl phenyl acetate, amyl salicylate, anethole synthetic, anisyl acetate, anisyl alcohol, anther, aubepine para cresol, benzyl acetone, benzyl butyrate, benzyl isobutyrate, benzyl isovalerate, benzyl propionate, bergamyl acetate, berryflor, boisiris, butyl butyro lactate, butyl cyclohexanol para, butyl cyclohexyl acetate para, butyl quinoline secondary, carvone laevo, caryophyllene, cashmeran, cedrene epoxide, cedroxyde, cedryl methyl ether, celery ketone, centifolyl, cetonal, cetone alpha, cinnamic aldehyde, cinnamyl acetate, citral dimethyl acetal, citrodyle, citronellol, citronellyl acetate, citronellyl butyrate, citronellyl formate, citronellyl isobutyrate, citronellyl nitrile, citronellyl oxyacetaldehyde, citronellyl propionate, clonal, coniferan, creosol, cresyl acetate para, cresyl isobutyrate para, cumin nitrile, cuminic aldehyde, cuminyl alcohol, cyclamen aldehyde extra, cyclogalbanate, cyclohexyl ethyl acetate, cyclohexyl salicylate, cyclomethylene citronellol, cyperate, damascenone, decahydro naphthyl formate beta, decalactone delta, decalactone gamma, decatone, decyl methyl ether, delphone, dihexyl fumarate, dihydro ambrate, dihydro cyclacet, dihydro eugenol, dihydro famesal, dihydro ionone beta, dihydro jasmone, dihydro linalool, dihydro terpineol, dimethyl anthranilate, dimethyl benzyl carbinol, dimethyl benzyl carbinyl acetate, dimethyl benzyl carbinyl butyrate, dimethyl phenyl ethyl carbinol, dimethyl phenyl ethyl carbinyl acetate, diphenyl methane, diphenyl oxide, dipropylene glycol, dupical, ebanol, ethyl caprylate, ethyl cinnamate, ethyl decadienoate, ethyl linalool, ethyl linalyl acetate, ethyl octenoate-2, ethyl pelargonate, ethyl phenoxy acetate, ethyl phenyl acetate, ethyl phenyl glycidate, ethyl salicylate, eugenol pure, eugenyl acetate, farnesene, fennaldehyde, fixambrene, floralozone, floramat, florol, floropal, folenox, folione, folrosia, fraistone, fructone, fruitate, gardenol, gardocyclene, georgywood, geraniol, geranitrile, geranitrile T, geranyl acetate, geranyl acetone, geranyl butyrate, geranyl crotonate, geranyl formate, geranyl isobutyrate, geranyl propionate, givescone, glycolierral, guaiyl acetate, gyrane, heliotropine crystals, hexenyl-3-cis benzoate, hexenyl-3-cis hexenoate, hexenyl-3-cis salicylate, hexenyl-3-cis tiglate, hexyl benzoate, hydroxycitronellal dimethyl acetal, indoflor, indole pure, indolene, ionone beta, irisantheme, irisone alpha, ironal, irone alpha, irone E, irone F, iso E super, isobomyl propionate, isobutyl benzoate, isobutyl phenyl acetate, isobutyl quinoline-2, isobutyl salicylate, isocaryol acetate, isoeugenol, jasmal, jasmin lactone delta, jasmin lactone gamma, jasmolactone, jasmone cis, jasmonyl, kephalis, kohinool, labienone, lactoscatone, lemarome N, lemonile, lierral, lilial, linalyl acetate, linalyl butyrate, linalyl formate, linalyl isobutyrate, linalyl propionate, lindenol, majantol, mayol, menthanyl acetate, metambrate, methoxy phenyl butanone, methyl acetophenone, methyl cinnamate, methyl cinnamic aldehyde, methyl decalactone gamma, methyl diantilis, methyl diphenyl ether, methyl ional beta, methyl isoeugenol, methyl octalactone, methyl octyl acetaldehyde, methyl octyne carbonate, methyl phenyl acetate, methyl quinoline para, moxalone, myraldene, neofolione, nerol C, neryl acetate, nonadyl, nopyl acetate, octahydro coumarin, octalactone delta, octalactone gamma, orcinyl 3, orivone, osyrol, oxyoctaline forrnate, parmavert, peach pure, pelargol, phenoxanol, phenoxy ethyl alcohol, phenoxy ethyl isobutyrate, phenyl ethyl acetate, phenyl ethyl alcohol, phenyl ethyl butyrate, phenyl ethyl forrnate, phenyl ethyl isobutyrate, phenyl propionic aldehyde, phenyl propyl acetate, phenyl propyl alcohol, pinoacetaldehyde, plicatone, precarone, prunolide, pyralone, radjanol, resedal, rhodinyl acetate, rhubafuran, rhubofix, rhuboflor, rosalva, sandalore, scentenal, skatole, spirambrene, stemone, strawberry pure, styrallyl propionate, syringa aldehyde, tangerinol, terpinene alpha, terpinyl acetate, terranil, tetrahydro linalyl acetate, tetrahydro myrcenol, tridecenonitrile, tropional, undecatriene, undecavertol, veloutone, verdol, verdyl acetate, verdyl propionate, vemaldehyde, vetynal, vetyvenal, and viridine, acetal CD, aldrone, ambrettolide, ambroxan, benzophenone, benzyl benzoate, benzyl cinnamate, benzyl phenyl acetate, cepionate, cetalox, citronellyl ethoxalate, civettone, cresyl caprylate para, cresyl phenyl acetate para, cyclohexal, diethyl phthalate, dione, dodecalactone delta, dodecalactone gamma, ethyl maltol, ethyl vanillin, ethylene brassylate, eugenyl phenyl acetate, evernyl, fixolide, florhydral, galaxolide, geranyl phenyl acetate, geranyl tiglate, grisalva, hedione, hexyl cinnamic aldehyde, hexyl salicylate, isomethyl cedryl ketone, laitone, linalyl benzoate, linalyl cinnamate, linalyl phenyl acetate, maltol, maltyl isobutyrate, methyl cedryl ketone, methyl dihydro isojasmonate, muscone, myraldyl acetate, nectaryl, okoumal, orange aldehyde, oranile, peonile, phenyl ethyl benzoate, phenyl ethyl cinnamate, phenyl ethyl phenyl acetate, propyl diantilis, rosacetol, rosaphen, sandela, thibetolide, timberol, triethyl citrate, undecalactone delta, vanillin, vanitrope, and velvione.

The reservoir is configured to receive a desired loading of fragrance material whilst leaving an appropriate volume about the fragrance material for a saturated head space of fragrance material to be generated in a short period of time, for example within a few seconds.

Preferably, the reservoir will have a volume of between 0.01 and 20 cm$^3$ in order to receive up to 5 mg to 5 grams of fragrance material whilst providing sufficient volume for a head space of 0.005 to 10 cm$^3$ depending on the carrier material. The upper limit on this head space is such as to permit of rapid re-saturation of the head space, e.g. within 10 seconds, more preferably 2 to 5 seconds after the previous head space is expelled on a stream of carrier gas. Its lower limit is dictated by the need to have sufficient fragrance in the gaseous phase to provide a powerful fragrance accord to a user.

The reservoir may simply contain fragrance oil. However, it is preferred if the reservoir contains a carrier material for receiving the fragrance oil. The use of the term "fragrance material" in this application encompasses both a fragrance alone and a fragrance in combination with a carrier material. Any carrier material can be employed that is porous and/or absorbent, and which is not active in respect of any of the components of the fragrance material, e.g. the carrier material preferably should not be selectively absorbent for certain fragrance material components. Preferably, such carrier materials are porous substrates that can accept high loadings of fragrance material.

Suitable carrier materials are the porous glass substrates described in U.S. Pat. No. 5,573,984 which is hereby incorporated by reference. Using said carrier material in the form of small porous glass-beads has the advantage that in practical considerations the ratio of the surface of the fragrance liquid is amplified by 2 orders of magnitude without being absorbed to an active surface. Furthermore, clogging cannot occur, a feature that is rather common in known systems using carrier materials in powdered form.

The porous glass beads described in U.S. Pat. No. 5,573,984 represent an excellent carrier material, but are relatively expensive. Other suitable materials include porous glasses available such as LiaVer® or Rheopore®, which after milling to the desired particle size and after a purification step to wash out any organoleptic materials such as sulphur-containing compounds used in the manufacture of the glasses, can be used in a similar manner as the porous glass beads described above. Other examples of suitable materials are the porous polyethylene and polybutylene polymers available commercially under the trade mark Porex®.

The cartridge should be formed of a self-supporting material that is capable of withstanding the pressure of carrier gas passing there through, and is also capable of withstanding any mechanical stresses associated with handling and storage. Preferably, it is formed of an inert material, i.e. one that does not react with, or adversely affect, the fragrance material. Most preferably the cartridge is formed of glass, silicon or a metal such as steel (preferably stainless steel) or aluminium which are commonly used to store fragrances in cartridges known in the art. It is also possible to use fragrance-compatible polymeric materials, or a combination of materials such as steel or glass lined internally with an inert polymeric layer.

Cartridges may be formed by a variety of techniques known in the art for producing 3-dimensional microstructures in quartz, metal, silicon and plastics materials. In a preferred embodiment, the cartridges are formed of unitary construction wherein the capillary and reservoir structures may be hollows formed in blanks of glass, metal, silicon and polymeric or plastics materials using, for example, using techniques such as hot-embossing or laser etching.

Once the structures have been formed in a suitable cartridge material, carrier material may be added to the reservoir and fragrance material dosed thereon, before the whole structure is sealed, for example by laser welding on to the structures a layer of compatible glass, silicon, metal (such as steel or aluminium) or fragrance-compatible polymeric or plastics material to form the finished cartridges. In this manner, one or a series of cartridges may be made from a single blank. Such manufacturing techniques enable cartridges to be mass-produced in a cheap manner. This represents an important advantage of the present invention as the cartridges are preferably designed as replaceable elements to be discarded after use, and as such they should be of simple and cheap construction. Furthermore, as the 3-D microstructures of the capillaries and reservoirs can be formed in this manner, the cartridges can easily be miniaturised.

If the cartridge blanks have sufficient mechanical strength, then one or a series of cartridges formed from the same blank may act as a self-supporting body. However, it may be preferable to laminate onto the cartridges with a suitable support material that may be formed of any suitable material such as plastics materials, or metals that are able to add a protective surface and additional mechanical strength to the cartridges. Accordingly, a support body containing cartridges forms another aspect of the present invention.

The support body is preferably formed of a plastics material for ease of manufacture, for example according to known moulding operation. The support body should be configured in order to accommodate one or a number of cartridges, in a manner that permits of their insertion or attachment into any suitable device containing a pump to provide carrier gas. Aside from this functional limitation to the configuration of the support body, it can have any fanciful design components that add to eye appeal. In a particularly preferred embodiment of the invention, the support body may be configured in the shape of a credit card. Furthermore, the support body may contain surface features such as printed matter that add information concerning the fragrances, advertisements, or decorative features. Still further, the support body may be provided with a machine-readable microprocessor chip. The chip may contain certain information regarding security that will prevent use of the fragrance material contained in the cartridge without tampering with and destroying the support body and cartridge. Furthermore, the chip may contain information that can be read by a pump in a device in order that the fragrance can be released from a cartridge or cartridges in a pre-determined sequence, that may be synchronised with an audio/visual display.

A cartridge, or support body containing a cartridge, according to the present invention may be fitted into, or connected with, a device comprising a pump. In a simple embodiment, it may simply be connected to a pump via a suitable conduit, e.g. a series of flexible pipes corresponding to the number of cartridges. The flexible pipes may terminate in ferrules, e.g. each having a male portion adapted to register in air-tight connection with the inlet ports of the cartridges. Carrier gas may thereafter be expressed down one or more pipes to emit a desired fragrance accord. A user may grasp the cartridges or support body and place its nose close to the outlet ports in order to smell the emitted fragrance. Alternatively, it is possible to connect a series of pipes in a similar manner to the outlet ports in order that the user can sense the fragrance at a position remote from the support body or cartridges.

Although there has been described a very simple means of operating the present invention for sensing fragrance accords, the skilled person will understand that there are many ways for the support body and/or cartridges to engage with a pump device in order to achieve a desired result. Some further and specific embodiments are described with reference to the drawings.

Having regard to the foregoing description of the invention, the skilled person will appreciate that the cartridges of the present invention are useful in a multitude of applications relating to the sensorial enhancement of audio and visual presentations. Thus the invention relates to methods and devices for enhancing the sensorial perception of audio and visual presentations using or comprising a cartridge and/or support body described herein.

Cartridges contained in a support body as described herein represent a convenient means of storing samples of fragrance materials. They are easy and cheap to prepare; mechanically tough and light, they are easy to handle and store. Furthermore, they are easily packaged and shipped and so may represent a considerably cheaper and more efficient means of perfumers supplying fragrance samples to clients. Clients thereby have a neat and convenient source of fragrance materials that are not of the liquid-in-vial type currently used and so are not prone to handling difficulties, or problems with contamination.

The cartridge and devices containing same or adapted to receive same are particularly useful for perfumers who want to present new accords to their customers. A simple, miniaturised and portable device containing a pump, can be provided that is adapted to receive a cartridge or cartridges contained on a suitable support. The cartridge holds a series of fragrance accords and is provided with a chip that is synchronised for a certain audio-visual displays. The device is attached to a customer's PC, and the cartridge is inserted into, or connected with, the device. Activation of an audio/visual display, that may be interactive for the users greater control, causes the cartridge chip to be read and for the pump to express carrier-gas through the appropriate cartridges in a pre-determined sequence.

The invention therefore also provides a device comprising means for receiving a cartridge or support body as hereinabove defined, containing a cartridge and passing carrier gas therethrough, and a conduit leading from the cartridge for carrying a stream of fragrance-containing carrier gas, the conduit having an outlet or outlets for presenting head space to a user.

BRIEF DESCRIPTION OF THE DRAWINGS

The invention will be further described with reference to the drawings, which depict non-limiting preferred embodiments.

DETAILED DESCRIPTION OF THE INVENTION

Figure 1A:
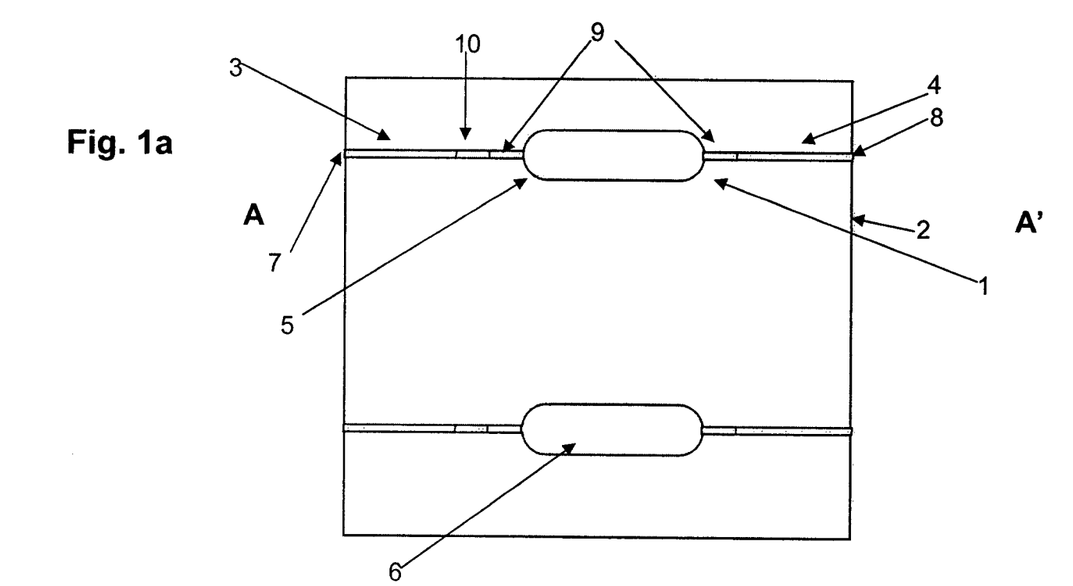
FIG. 1a is a plan view of a support body bearing two cartridges.
Figure 1B:
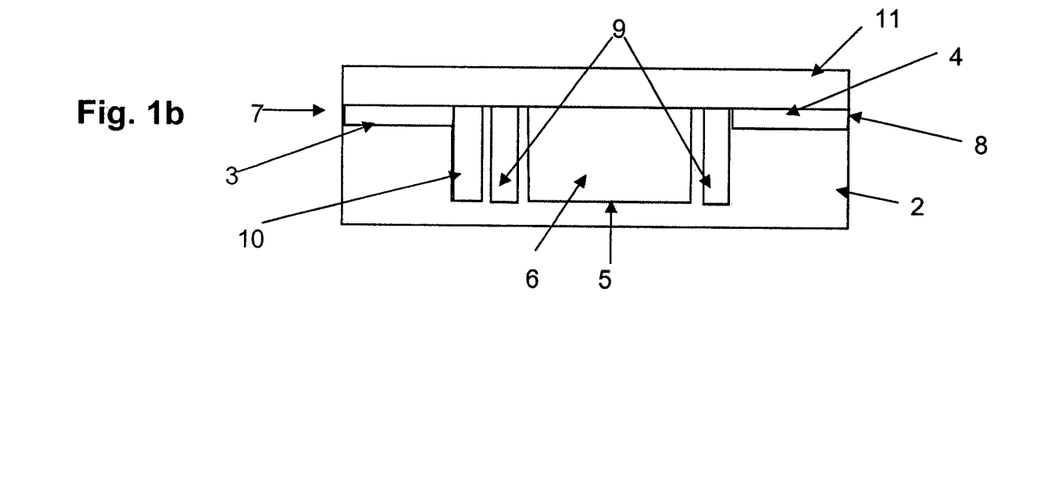
FIG. 1b is a longitudinal cross-section of the embodiment of FIG. 1a along the line AA'.

The cartridge depicted in FIGS. 1a and 1b is a generally elongate body (1) consisting of an inlet capillary (3) and an outlet capillary (4) each connecting at one terminus with a reservoir (5), the reservoir containing a porous and/or absorbent material (6) for holding a fragrance material. At the other terminii of the capillary are respectively inlet port (7) and outlet port (8) for permitting ingress of carrier gas and egress of fragrance-containing carrier gas respectively. Inlet and outlet capillaries contain filters (9) intended to prevent fragrance material, substrate material or any other particulate matter from being carried from the reservoir and carried out of the cartridge via the inlet and outlet capillaries. Additionally, inlet capillary (3) is equipped with an active carbon filter (10) in order to remove any organoleptic material carried into the cartridge by the carrier gas.

Each cartridge is sealed with a sealing layer (11). Sealing may be achieved by laser welding an appropriate material on to the support (2).

Whereas in this embodiment each of the outlet capillaries are provided with separate outlet ports, in an alternative embodiment the outlet capillaries may converge in a manifold-type arrangement such that all outlet capillaries share a common outlet port.

Figure 2A:
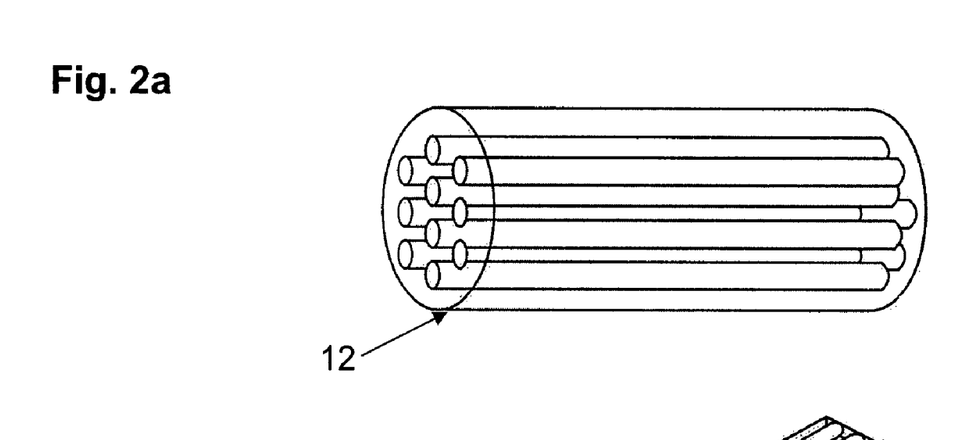
FIG. 2a is a schematic perspective view of a support body containing a plurality of cartridges within the support body.

FIG. 2a shows a generally cylindrical support body (12) containing a plurality of cartridges internal of the support. Details of the cartridge are left out for ease of representation.

Figure 2B:
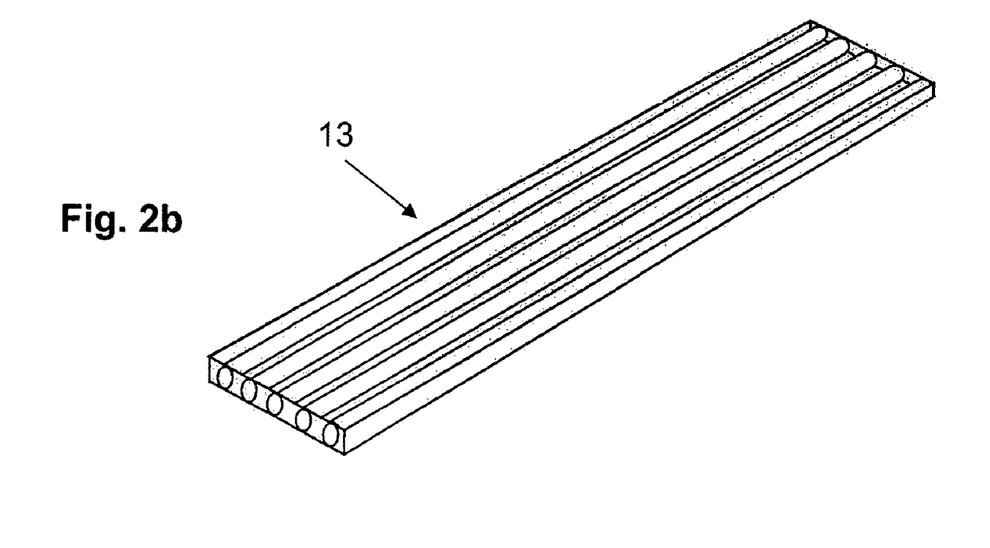
FIG. 2b is a schematic perspective view of another type of support body, this one in the preferred credit card format.

FIG. 2b shows a preferred credit-card design for a support body (13) in perspective containing a plurality of cartridges the details of which are not shown.

Figure 3A:
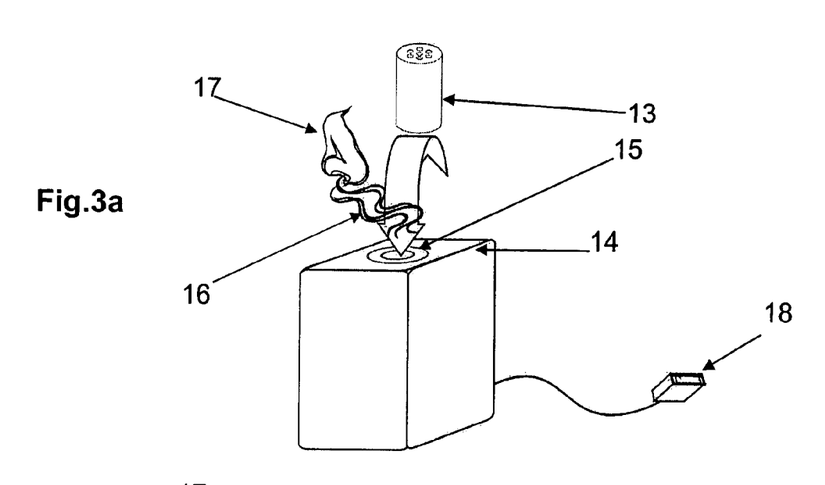
FIGS. 3a and 3b are schematic representations of the loading of the support bodies of FIGS. 2a and 2b into devices.
Figure 3B:
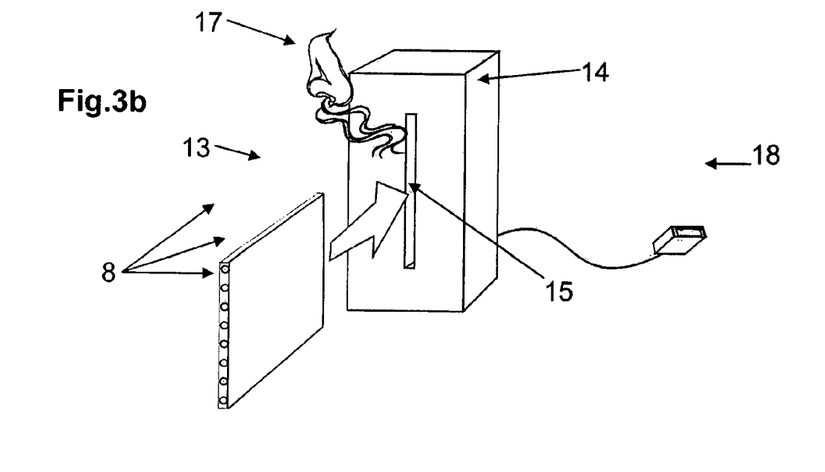

FIGS. 3a and 3b depict the support bodies of FIGS. 2a and 2b, that are in the process of being inserted into a device (14) along the direction of the arrow into an orifice (15). Once inserted into the device, the inlet ports of the cartridges align with and register in substantially air-tight communication with capillaries extending from a pump means (not shown). A readable microprocessor chip (not shown) on an outer surface of the support body (13) can be read by the device such that, when the device is activated, pump means will express carrier gas into the inlet capillary of an appropriate cartridge according to a pre-determined sequence that may be synchronised with a visual or acoustic performance. In this simple arrangement, outlet ports (8) of the cartridges express fragrance-containing carrier gas (16) into a head space immediately surrounding the orifice, where it can be detected by a user (17). Of course, outlet capillaries can be connected to conduits (not shown) that can carry the fragrance-containing carrier gas to a position remote from the device, where a user can sense the fragrance material emanating into a head-space local to the outlet of the conduits. Socket (18) may be a simple plug for connecting the device to a source of power such as a mains supply or a battery. Alternatively, socket may be a USB connector for connecting the device to a computer terminal or other electronic device such as a television or the like. Alternatively, socket may be a Blue Tooth® connector or alternative wireless connector to permit of radio transmission means of activating the device.

Figure 4:
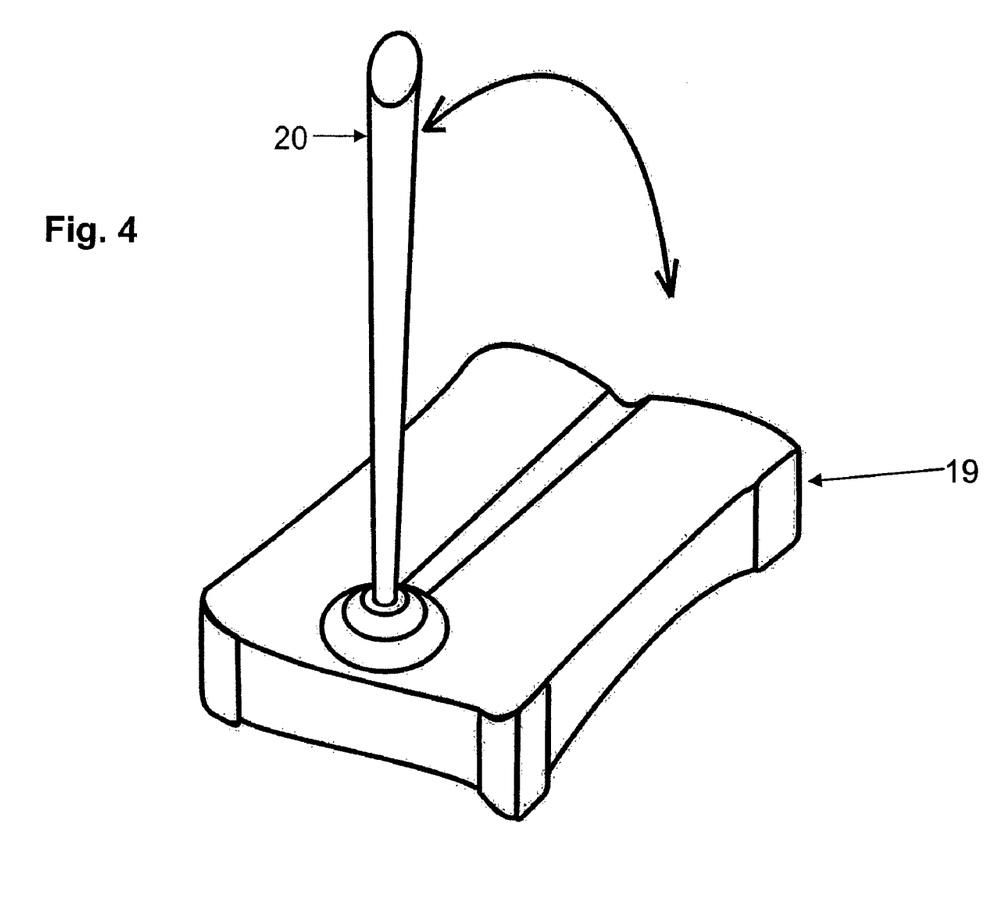
FIG. 4 is a perspective view of a device for use with cartridges acording ton this invention.
Figure 5:
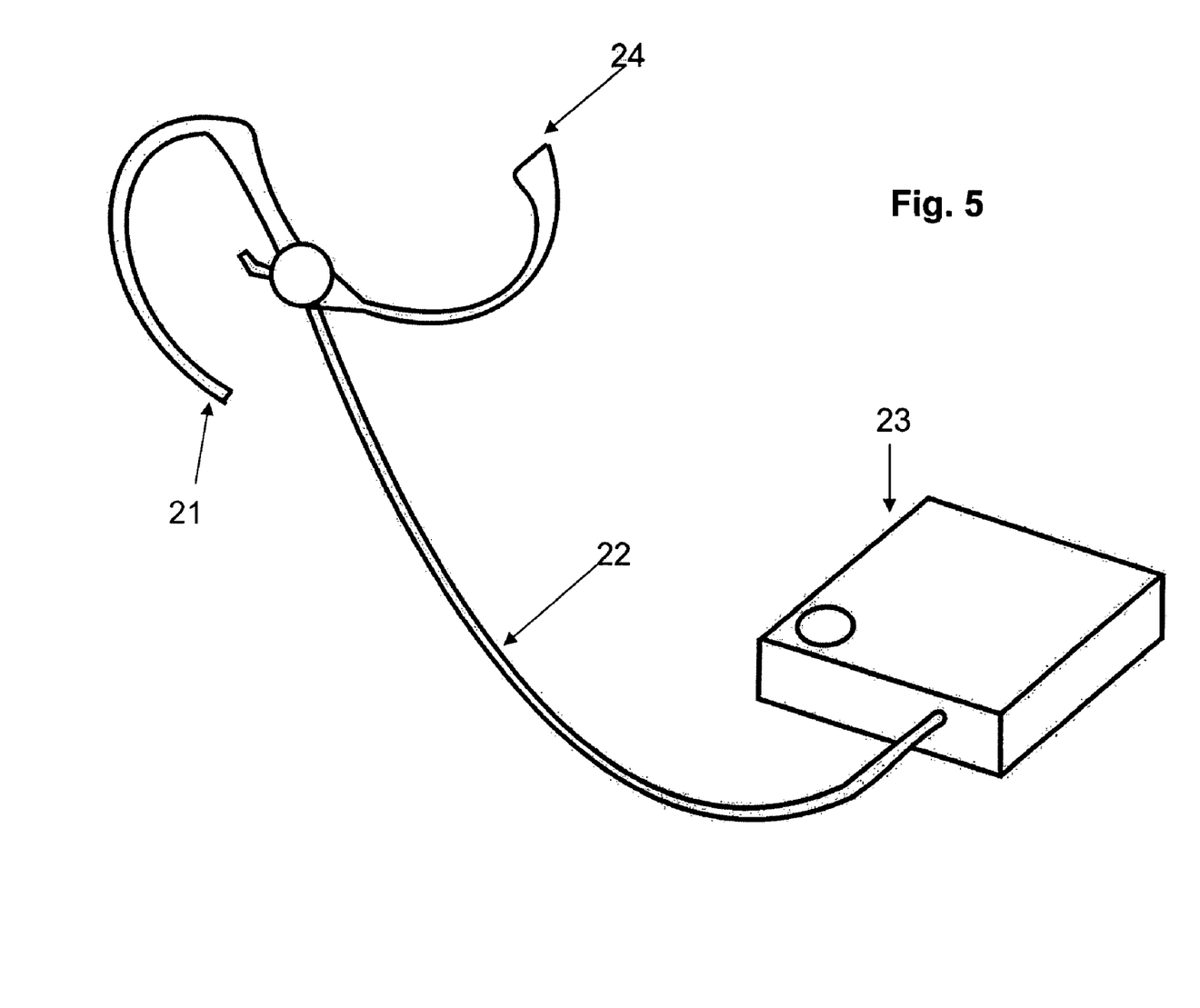
FIG. 5 is a perspective view of an alternative device for use with cartridges according to this invention.

FIG. 4 shows a device (19) containing a pivotally-mounted conduit (20) that is connected internally to outlet capillaries of a cartridge contained in the device such that the fragrance emitted from the cartridge can be sensed by the user remote from the device. FIG. 5 shows an alternative design variant whereby remote sensing of fragrance material is achieved by a head-set arrangement (21) having a conduit (22) connected to a cartridge contained in a device (23), the conduit being fixed at one end to the head-set such that, in use, the outlet (24) of the conduit is positioned under the nose of a user wearing the head set.

The invention claimed is:

1. A fragrance cartridge comprising
at least one reservoir including a carrier material for containing a fragrance material;
a capillary ingress channel and a capillary egress channel, both channels being connected to the at least one reservoir and both channels include filters,
a carrier gas being connected to provide carrier gas upon demand into the ingress channel,
the egress channel being adapted to allow the carrier gas to escape after passing the fragrance material of the reservoir,
the capillary ingress and the capillary egress channels being defined by capillaries having internal diameter and length dimensions sufficient to act as closure means to substantially prevent leakage of fragrance from the reservoir into a head space external of the cartridge when there is no demand of carrier gas.

2. The cartridge according to claim 1, wherein the capillaries independently have a diameter of 0.1 to 0.4 mm.

3. The cartridge according to claim 1, wherein the capillaries independently have a length of 20 to 30 mm.

4. The fragrance containing cartridge according to claim 1, wherein fragrance leakage does not exceed a rate of 400 ng per second.

5. The cartridge according to claim 1, wherein the filters included in the capillary ingress channel and the capillary egress channel includes are active carbon filters.

6. A fragrance cartridge comprising
a first reservoir being adapted for containing a first fragrance material;
a first capillary ingress channel and a first capillary egress channel, both first capillary channels being connected to the first reservoir,
a carrier gas being connected to provide carrier gas upon demand into the first capillary ingress channel,
the first capillary egress channel being adapted for the carrier gas to escape after passing the first fragrance material of the reservoir,
a second reservoir being adapted for containing a second fragrance material,
a second capillary ingress channel and a second capillary egress channel, both second capillary channels being connected to the second reservoir,
a carrier gas being connected to provide carrier gas upon demand into the second capillary ingress channel,
the second reservoir is independent of the first reservoir,
the second capillary egress channel being adapted for the carrier gas to escape after passing the second fragrance material of the reservoir,
the first and second capillary ingress and capillary egress channels being defined by capillaries having internal diameter and length dimensions sufficient to act as closure means to substantially prevent leakage of fragrance from the reservoir of the cartridge when there is no demand of carrier gas and wherein the cartridge is a unitary construction formed of one of glass, metal, silicon, polymeric or plastic material.

7. The cartridge according to claim 6, wherein the at least one reservoir includes carrier material made of porous and/or absorbent material.

8. A support body having embedded therein a cartridge or cartridges according to claim 6.

9. The support body according to claim 8, comprising a substantially flat body in the shape of a credit card, wherein the first ingress channel and the first egress channel and the second ingress egress channel and the second egress channel are formed as hollows provided by hot- embossing or laser etching.

10. A support body according to claim 9, having on an outer surface a machine-readable microprocessor chip containing instructions to be read by a device regarding actuation of gas flow through the cartridge or cartridges in a time-dependent and sequential manner, optionally relaying signals from audio or visual apparatus thereby to synchronize the presentation of odours with an audio and/or visual display.

11. The support body according to claim 8, further comprising a machine readable chip.

12. A device comprising a pumping means for expelling carrier gas and a cartridge, cartridges, or support body containing a cartridge or cartridges according to claim 1.

13. A method of enhancing the sensorial perception of a viewer, listener or consumer of an audio and/or visual performance or presentation comprising the step of
passing carrier gas through a cartridge, support body or device according to claim 1, thereby to present fragrances into a head space local to the listener, viewer or consumer.

* * * * *

UNITED STATES PATENT AND TRADEMARK OFFICE
CERTIFICATE OF CORRECTION

PATENT NO.       : 7,601,297 B2  
APPLICATION NO.  : 10/521716  
DATED            : October 13, 2009  
INVENTOR(S)      : Gygax et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 359 days.

Signed and Sealed this

Fifth Day of October, 2010

David J. Kappos  
*Director of the United States Patent and Trademark Office*